United States Patent [19]
Vielkind

[11] Patent Number: 6,057,116
[45] Date of Patent: *May 2, 2000

[54] MELANOMA AND PROSTATE CANCER SPECIFIC ANTIBODIES FOR IMMUNODETECTION AND IMMUNOTHERAPY

[75] Inventor: Juergen R. Vielkind, Vancouver, Canada

[73] Assignee: Research Corporation Tech., Inc., Tucson, Ariz.

[*] Notice: This patent is subject to a terminal disclaimer.

[21] Appl. No.: 08/869,285

[22] Filed: Jun. 2, 1997

Related U.S. Application Data

[63] Continuation-in-part of application No. 08/654,641, May 28, 1996, Pat. No. 5,719,032, which is a continuation-in-part of application No. 07/829,855, Jan. 31, 1992, Pat. No. 5,605,831.

[51] Int. Cl.[7] .................................................. G01N 33/53
[52] U.S. Cl. ......................... 435/7.23; 435/7.2; 530/350; 530/387.7; 530/387.9; 530/391.3
[58] Field of Search ..................... 435/7.2, 7.23; 530/387.7, 387.9, 388.8, 391.3, 350

[56] References Cited

U.S. PATENT DOCUMENTS 4,590,071  5/1986  Scannon et al. ................. 424/183.1
5,162,504  11/1992  Horoszewicz ................. 530/388.2

OTHER PUBLICATIONS

Hird et al., *Genes and Cancer* (1990) 183–189.
Sevier, et al., *Clin. Chem.* (1981) 27:1797–1806.
Wittbrodt, et al., *Nature* (1989) 341:415–421.
Parker, et al., *Biochemistry* (1986) 25:5425–5432.
Lerner, et al., *Nature* (1982) 299:592–596.
Staerz and Bevan, *Proc. Nat. Acad. Sci.* (1986) 83:1453–1457.
Waldmann, *Science* (1991) 252:1657–1662.
Real et al., *Cancer Research* (1986) 46:4726–4731.
Carrasquillo, *Cancer Treatment Reports* (1984) 68:317–328.
Gown, et al., *The American J. Pathology* (1986) 123:195–203.

Primary Examiner—Paula K. Hutzell
Assistant Examiner—Minh-Tam Davis
Attorney, Agent, or Firm—Scully, Scott, Murphy & Presser

[57] ABSTRACT

Methods and compositions are provided for detecting antigens having a specific epitope associated with melanoma and prostatic carcinoma. The epitope is present in melanoma cells and prostatic cancer cells but is essentially absent from melanocytes and normal prostatic tissue. The antibody can be used in diagnostic methods for histochemical detection of human melanoma and prostate carcinoma, of various progression stages and in treatment of melanoma and prostate carcinoma.

5 Claims, 5 Drawing Sheets

FIG. 1c  L F R S E D Q S I E = LeuPheArgSerGluAspGlnSerIleGlu

MELANOMA AND PROSTATE CANCER SPECIFIC ANTIBODIES FOR IMMUNODETECTION AND IMMUNOTHERAPY

CROSS-REFERENCE TO RELATED APPLICATIONS

This application is a continuation-in-part of U.S. Ser. No. 08/654,641, filed May 28, 1996, now patented, U.S. Pat. No. 5,719,032, which is a continuation-in-part U.S. Ser. No. 07/829,855 filed Jan. 31, 1992, now U.S. Pat. No. 5,605,831, which disclosures are herein incorporated by reference.

INTRODUCTION

1. Field of Invention

The subject invention is related to the use of antibodies, which bind to a unique peptide obtainable from a Xiphophorus melanoma mrk-receptor tyrosine kinase for the diagnosis and therapy of melanoma and prostate cancer.

2. Background

The ability to detect and diagnose cancer through the identification of tumor markers is an area of widespread interest. Tumor markers are substances, typically proteins, glycoproteins, polysaccharides, and the like which are produced by tumor cells and are characteristic thereof. Often, a tumor marker is produced by normal cells as well as by tumor cells. In the tumor cells, however, the production is in some way atypical. For example, production of a tumor marker may be greatly increased in the cancer cell. Additionally, the tumor marker may be released or shed into the circulation. Detection of such secreted substances in serum may be diagnostic of the malignancy. Therefore, it is desirable to identify previously unrecognized tumor markers, particularly, tumor markers which are secreted into the circulation and which may be identified by serum assays. It is also desirable to develop methods and compositions which allow determination of the cellular origin of a particular tumor or other proliferative disease, for example by radioimaging techniques. The location of the tumor markers on the surface of the cells, particularly where there is an extracellular domain that is accessible to antibodies (i.e., the domain acts as a receptor for the antibodies), provides a basis for targeting cytotoxic compositions to the receptor. Examples of compositions of interest in such a method include complement fixing antibodies or immunotoxins which bind to the receptor as a means of specifically killing those cells which express the receptor on the cell surface.

Human malignant melanoma arises from a series of stages starting with the harmless mole, going through intermediate stages of radial to invasive growth and ending in the destructive final stage of metastatic melanoma. Melanoma usually resists chemotherapy as well as radiotherapy. Surgery is the most effective treatment. However, for it to be effective, surgery requires early diagnosis which is unfortunately hampered by the lack of accurate markers for melanoma. Melanoma associated antigens have been found, but they are of little diagnostic value. For example, the nerve growth factor receptor is found in high density on melanoma cells. However, monoclonal anti-nerve growth receptor antibodies are specific for neural crest cell diseases rather than for melanoma alone. Likewise, other melanoma associated antigens against which antibodies have been raised are nonspecific for melanoma cells. Examples are the monoclonal antibodies raised against in vitro grown melanoma cells which are directed against gangliosides or glycoproteins present on the melanoma cells. Both antigens are also found on other cells.

Adenocarcinoma of the prostate is one of the most common tumors in men and accounts for 10% of deaths from malignant disease in males in the United States. Only a small proportion of these cases becomes clinically apparent prior to death, the remainder being latent carcinoma. Radical prostatectomy remains the treatment of choice for tumors confined to the gland but this is applicable to only a tiny fraction of cases. Orchiectomy and hormone therapy (usually estrogen therapy) together appear to be the most effective palliative treatment in patients with symptomatic cancer of the prostate and are also used as an adjunct to surgery. However, there are significant side effects to the use of estrogens, including an increase in mortality from cardiovascular disease.

Three-fourths of the tumors arise in the posterior lobe, and urinary symptoms therefore tend to occur late in the disease. The identification and isolation of cancer genes, most notably demonstrated for colon carcinoma, has been a major breakthrough for our understanding of tumorigenesis. Cancer is basically a disease of multiple genetic changes resulting in stages of progression of a normal cell into a highly malignant, metastasizing cell.

However, very little is known about the development and clinical progression of prostatic carcinoma at the genetic level. Studies of familial clustering of prostate cancer have provided evidence for a rare, high risk autosomal dominant allele which may be responsible for early onset of prostate cancer (Carter B. S., et al., *Proc. Natl. Acad. Sci USA* 89:3367–3371, 1992; Carter B. S., et al., *J. Urol.* 150:797–802, 1993). Indeed a consortium of several research groups has recently localized a major prostate cancer susceptibility locus on the long arm of chromosome 1 (1q24–25) (Smith R. J. et al., *Science* 274:1371–1373, 1996). In addition, several chromosomal alterations such as gain of 8q and loss of 8p (Visakorpi T. et al., *Cancer Res.* 55:342–347, 1995; cher M. L. et al., *Cancer Res.* 56:3091–3102, 1996) as well as loss of 10q, 13q, 16q, 17p (Isaacs W. B., et al., *Cancer Surveys* 23:19–32, 1995; Cher M. L. et al., *Cancer Res.* 56:3091–3102, 1996) and 11p11.2 (Dong, J. T., et al., *Science* 268:884–886, 1995) have been identified. Similarly, the group at the Mayo Clinic (Qian et al., 1995) using fluorescence in situ hybridization has shown gains of chromosome 7, 8, 10 and 12 and detected similar proportions of anomalies in PIN and carcinoma supporting the notion that PIN is the supposed precursor lesion. This study showed also that the gain of chromosome 8 was the most common alteration and mostly correlated with the cancer grade. This amplification of chromosome 8 genes may lead to overexpression and could play a key role in progression of prostatic carcinoma.

A significant number of patients come into the physician with symptoms due to distant metastases. Cancer of the prostate arises through a continuum from normal luminal secretory cells which progress through a dysplastic stage of mild to severe prostatic intraepithelial neoplasia (PIN) to carcinoma in situ and invasive carcinoma cells. PIN is considered the precursor stage; however, once grade 3 is reached, the cancer enters a malignant stage which is characterized by cells breaking loose from the epithelium and invading the neighboring stromal component of the prostate gland. This invasion takes place where the basal cell layer is disrupted and the basement membrane is fragmented. The cancer cells then progress from well, to moderately and finally poorly differentiated cells. These cells, staged according to Gleason grades 1–5, are believed to reflect the increasing aggressiveness of the cancer of the prostate.

Frequent routine rectal examinations are the best means of demonstrating early and operable prostatic tumors. Measurement of prostate specific antigen as a screening test for prostate cancer has been used but presents both technical difficulties and a high false positive rate. Prostatic acid phosphatase also has been used as a marker for prostate cancer but does not detect all cancers. The most successful detection of prostate cancer is from the combined use of a digital rectal exam, transrectal ultrasound and detection of prostate specific antigen. The sensitivities of the three tests individually vary from 50% to 85% but the positive predictive value fluctuates around 30%. When these three investigations are summated, the detection rate is approximately twice as high as when a single parameter is used. The only reliable procedure for definitive diagnosis of prostatic carcinoma is by open perineal biopsy. Needle biopsies and cytologic studies of prostatic fluid are unreliable for the diagnosis of early cancer but are useful methods of obtaining a histological diagnosis in the more advanced cases. It therefore is of interest to identify in particular, early stage prostatic cancer and to identify non-invasive methods of treating prostatic cancer. It also is of interest to identify a melanoma-associated antigen which is specific for melanoma as compared to normal melanocytes as well as other normal and malignant cells. An antibody raised against such an antigen can be used in the diagnosis and treatment of melanoma. The antibody itself or an immunotoxin may find use as an antiproliferative agent. So far no single gene has been shown to be implicated in the genesis of prostate carcinoma. Once such genes are identified and characterized this will provide important insight into the development of this disease. In a larger frame work, it may then be possible to identify individuals at high risk and to predict whether or not an indolent tumor has the potential to become malignant. This may lead to new avenues for treatment of the disease.

Relevant Literature

U.S. Pat. No. 4,590,071 is directed to a cytotoxic conjugate specific for human melanoma Maguire, et al., *Cancer* (1993) 72:(11 Suppl.) 3453–62, disclose use of an antigen expressed by the majority of adenocarcinomas for preparation of immunoscintigraphic agents for the preclinical staging of prostatic carcinoma in patients with negative or equivocal results on standard imaging tests. Lopes, et al., *Cancer Research* (1990) 50:6423–9, disclose a prostate-reactive monoclonal antibody. Horoszewicz (U.S. Pat. No. 5,162,504), discloses monoclonal antibodies to an antigen on prostatic epithelial cells. U.S. Pat. No. 5,605,831 discloses a monoclonal antibody which binds to an epitope which is present on human melanoma cells and absent from melanocytes and malignant cells other than melanoma and prostatic cancer cells.

In the Xiphophorus fish melanoma model several genetic loci have been identified which mediate melanoma formation (see Vielkind, J. R. (1992) in *Transformation of Human Epithelial Cells: Molecular and Oncogenic Mechanisms*, Milo G E, Casto B C, Shuler C F, (eds), CRC Press). A duplicated gene, Xmrk, that genetically maps to an oncogenic locus has been cloned. The gene encodes a novel growth factor receptor tyrosine kinase which has similarities to the epidermal growth factor receptor (EGFR); its expression correlates with active melanoma growth (Woolcock et al., (1994) *Cell Growth Diff* 5:575–583). Overexpression of Xmrk results in autophosphorylation of the Xmrk protein in fish melanomas and cultured melanoma cells as well as in cultured fish, mouse and human cells transfected with a high expression CMV-Xmrk construct (Wittbrodt et al., (1992) *EMBO J.* 11:4239–4246).

SUMMARY OF THE INVENTION

The present invention provides methods and compositions useful for detecting or monitoring primary and metastatic melanomas and prostatic carcinomas. The methods use an antibody which is specific for epitope on the surface of melanoma and prostatic cancer cells. The antibody is produced using an immunogen comprising a unique sequence derived from a Xiphophorus melanoma. The epitope can be detected on the carcinoma cells in tissue biopsies, in carcinoma cells in culture, as well as in blood samples. The epitope appears to be located on the surface of the melanoma and prostatic carcinoma cells and may be a cell surface receptor. The putative receptor has an apparent molecular weight of 170 KD by western blotting of lysates of a melanoma cell line. Detection of the epitope conveniently is accomplished by reaction with monoclonal antibodies (XMEL) derived from hybridoma cell line 12f3.2, or antibodies having a similar specificity, and detecting the formation of specific antigen-antibody complexes. The antigens and/or antibodies find use in vitro or in vivo in diagnosis, prognosis and therapy. Antiidiotypic antibodies and the antigenic peptide also find use for detecting the presence of antibodies to the antigen in the blood or serum of a human host.

BRIEF DESCRIPTION OF THE DRAWINGS

FIG. 1. FIG. 1C shows the nucleotide sequence (SEQ ID NO:2) and amino acid sequence (SEQ ID NO:3) spanning the amino acid sequence from 446–486.

FIG. 2 shows immunostaining of cross-sections from a common acquired nevus (FIGS. 2A and 2B); a primary (vertical growth phase) melanoma (FIGS. 2C and 2D); and melanomas metastatic to the skin with the monoclonal antibody XMEL (FIGS. 2E and 2F and FIGS. 2G and 2H).

FIG. 4 shows XMEL immunostaining of prostatic carcinoma

DESCRIPTION OF SPECIFIC EMBODIMENTS

Figure 1A:
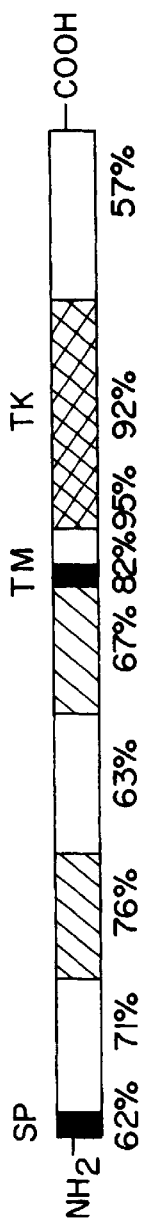
FIG. 1A shows a schematic structure of putative mrk receptor tyrosine kinase, SP=signal peptide, TM=transmembrane domain, TK=tyrosine kinase domain, striped boxes=cystine-rich domains, below similarities of various domains to the human epidermal growth factor receptor HER-1 (Wittbrodt, et al., (1989) *Nature* 341:415–421)

In accordance with the subject invention, methods and compositions are provided for the detection, identification, monitoring and treatment of carcinomas, especially melanomas and prostatic tumors, including high grade prostatic intraepithelial neoplasia (PIN). In melanomas, an about 170 KD protein is present on the cell surface of the cancer cells which is immunologically related to an mrk-receptor tyrosine kinase present in the Xiphophorus fish melanoma. Patient samples are screened for tumor cells by assaying for the presence of this cell surface protein in patient samples, including tissue biopsy specimens and blood samples; the receptor apparently is "shed" into the bloodstream.

Current clinical methods of predicting pathologic tumor stage of prostatic carcinoma, preoperatively, are extremely limited. Criteria such as pathologic stage, PSA level, histologic grade (well and poorly differentiated cancer cells, Gleason grade), tumor volume and percent of tumor are important prognosticators; however, they do not absolutely predict outcome of the tumor for the individual patient (see Humphrey, P. A., Walther P. J., *Am. J. Clin. Pathol* 100:256–269, 1993). Furthermore, determination of DNA content in prostatic cancer cells by flow cytometry also does not seem to predict clinical outcome (Jones E. C. *J. Urol* 144:89–93, 1990). Thus, although histopathological prognosticators are helpful, they only indicate trends and likelihood of the outcome. The current invention offers the advantage that it provides valuable prognostic information not available from current clinical methods. Because the 170 KD protein is on the cell surface, it is readily accessible to an antibody for detection of cancer cells in a tissue sample or for treatment of cancer cells. Also, it is easier for a surface protein than a cytoplasmic protein to shed into the blood stream, which provides a serum marker for detection of cancer. A serum assay for detecting of a cancer marker is a non-invasive method, which is more acceptable to patients and also provides a tool for screening large number of samples. Additional advantages include that the antibody recognizes an antigen that is related to the early events (primary melanomas) rather than the later stages of progression to the metastatic phenotype (metastatic melanomas). The antibody recognizes PIN, as well as prostate cancer cells. The antibody thus provides a tool for early detection of melanoma and prostate carcinoma. The antibody shows little or no cross-reactivity with normal tissues, either melanocytes or prostatic tissue and thus can provide accurate information regarding tumor location and provide a means for targetting cancer cells.

The Xiphophorus fish melanoma model is well established as a model for human malignant melanoma. In both, the melanomas are made up of the same cell type and are of the same developmental origin, the neural crest. The stages of melanoma progression which have been characterized for melanomas in humans are similar to those found in fish. One particular type of human melanoma, familial subcutaneous malignant melanoma is clustered in families, thereby indicating a genetic basis. Genes identified in the fish as being relevant to pigment cell development and/or melanoma formation can therefore be used as probes to isolate the human counterpart from genomic or cDNA libraries. Genes also can be used in raising antibodies against antigens found on human melanoma cells.

Several genetic factors can be identified which mediate the progression of a normal melanin-bearing pigment cell into a malignant, metastatic melanoma cell. One complex locus encompasses genetic information for the formation and location of macromelanophores and also for melanoma permissiveness; the term "macromelanophore" refers to the large melanophores found in Xiphophorus which are larger and have more melanin pigment than melanocytes in the human. To identify oncogene related genes on the chromosome carrying the complex locus, the Xiphophorus fish genome can be screened with conserved oncogene probes. Genetic linkage analysis is then used to identify genes which are closely linked to the complex locus and thus a candidate for any of the encoded information in the complex locus, for example, for melanoma permissiveness, and then to differentially screen for those genes found only in cells which produce the pigment cell giving rise to melanomas. Examples of such genes are the erb-B related gene, and the src (Rous sarcoma virus) oncogene. Genomic and cDNA clones are isolated and partially sequenced; and RNA expression studies carried out to identify genes which are preferentially expressed in tissue containing melanophores and which are highly expressed in the fish melanomas. Using this methodology genes which are specific for melanomatosis pigment cell growth can be identified. The gene product, or a portion thereof then is used to generate monoclonal antibodies. In order to obtain a highly specific antibody, the deduced amino acids encoded by the gene can be evaluated to identify a portion of the expression product most likely to be highly antigenic such as the extracellular domain of a surface receptor. DNAs encoding the human mrk protein from melanoma and from prostate cancer can be identified in a variety of ways. For example, genomic or cDNA libraries from prostatic cancer cells are screened with detectable enzymatically- or chemically-synthesized probes, which can be made from DNA, RNA, or non-naturally occurring nucleotides, or mixtures thereof. Probes may be enzymatically synthesized from DNAs from the Xmrk-protein for normal or reduced-stringency hybridization methods. Oligonucleotide probes also can be used to screen prostatic cancer and melanoma cells and can be based on sequences of known epidermal growth factor receptors, including conserved sequences, or on peptide sequences obtained from the purified protein. Hmrk protein from prostatic cancer and melanoma cells. Oligonucleotide probes based on amino acid sequences can be degenerate to encompass the degeneracy of the genetic code, or can be biased in favor of preferred human codons. Oligonucleotide probes encoding a consensus sequence which includes the amino acids DFPAL is preferred. Oligonucleotides also can be used as primers for PCR from reverse transcribed mRNA from prostatic cancer cells or melanoma cells; the PCR product can be the full length cDNA or can be used to generate a probe to obtain the desired full length cDNA. Alternatively, the Hmrk protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base composition, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA can also be employed.

The sequence also can be evaluated to identify a unique amino acid sequence, i.e., a portion of the polypeptide which is not found in other proteins using data bank comparisons and computer modeling. A peptide containing the amino acid sequence and optionally any additional residues desirable for coupling to a carrier for immunization is then prepared. The oligopeptides combine the desired amino acid sequences in substantially pure form. Thus, usually the subject composition is at least 80 mole percent, usually at least about 90 mole percent of the particular oligopeptide or mixture of oligopeptides which come within a particular formula.

The subject compounds are made in conventional ways which can be employed for the production of oligopeptides. Techniques include using automatic peptide synthesizers, employing commercially available protected amino acids. Alternatively, recombinant DNA technology may be employed, by synthesizing according to conventional procedures the appropriate nucleotide sequence, joining the sequence to an appropriate replication vector, transforming a host cell and cloning and growing the transformed host cell to produce the oligopeptides of interest which may then be isolated.

For preparation of antibodies, the subject compounds are conjugated to an immunogenic carrier, for example antigen proteins, to act as a hapten for production of antibodies specific for an epitope on melanoma or prostatic carcinoma cells. Various proteins are employed as antigens which are not endogenous to the host. Commonly employed antigens are the albumins, globulins, keyhole limpet hemocyanin, or the like. Haptenic conjugates to antigens are well known in the literature under and are amply exemplified in a wide variety of patents. See for example, U.S. Pat. Nos. 4,156,081, 4,069,105 and 4,043,989.

The haptenic antigen conjugates are used in accordance with conventional ways to immunize a mammal, for example, rat, mouse or higher mammal, for example, primate, including human in accordance with conventional procedures. See, for example, U.S. Pat. Nos. 4,172,124, 4,350,683, 4,361,549, and 4,464,465. Monoclonal antibodies can be produced as a result of hybridoma formation and expression by the hybridoma whether in culture or present as ascites. Hybridomas are prepared by fusing available established myeloma lines, for example, SP2-0, NS/1, AG8.6.5.3, etc. with peripheral blood lymphocytes, for example, splenocytes or other lymphocytes of the immunized host. The monoclonal antibodies can be any mammalian species, including murine, rabbit, human or the like, or combinations thereof, such as chimeric antibodies, having a human constant region and a mouse or other mammalian source variable region. The antibodies can be any class or subclass, such as IgA, IgD, IgG, IgM, and may include IgG1, 2a, 2b, or 3 or the human equivalents thereof. Methods for preparing monoclonal antibodies are well established. See, for example, *Monoclonal Antibodies,* eds. Roger H. Kennett, Thomas J. McKearn, Kathleen B. Bechtol, Plenum Pres,s New York, 1980; *Nature* (1975) 256:495–497; U.S. Pat. Nos. 4,271,145; 4,196,265; 4,172,124; 4,195,125; 4,262,090; and 4,294,927. A monoclonal antibody fragment, such as Fab, F(ab)'$_2$, Fv, a recombinant variable region, or the like may also find use. The resulting immortalized B-lymphocytes, for example hybridomas, heteromyelomas, EBV transformed cells etc., are then selected, cloned and screened for binding to the subject epitope.

Screening for antibodies which have the desired specificity can be performed using any of a variety of methods. For example, cultured cells that express a protein epitope on the cell surface are incubated with radiolabelled antibody at various dilutions in the presence or absence of unlabelled antibody. Following removal of the incubation medium and washing of the cells, the cells are treated with detergent, such as 0.1% SDS, to solubilize the bound protein and aliquots of the resulting solution are counted. The counts from the cultures incubated with both radiolabelled and unlabelled antibody are subtracted from the corresponding cultures containing only labelled antibody. The data then are analyzed, for example, using non-linear, least squares, curve fitting routine as provided by the program Systat 5.2, to obtain the apparent affinity constant and number of binding sites. Alternatively, flow cytometry and immunocytochemistry can be used to identify the binding of antibody to cells which express the epitope on their cell surface. Confirmation that a particular antibody is binding to the outside of the cell is obtained by immunohistochemical studies, wherein staining is limited to the outer surface of the cells.

The subject immortalized B-lymphocytes or other cells, for example T-cells, which provide receptors specific for the subject epitope, can be used as a source of DNA, either genomic or cDNA, for expression of the ligand heavy chains of the receptors in prokaryotes or eukaryotes. The resulting products may then be used as receptors for binding to the subject epitopes.

The epitopes are characterized as being present on melanoma cells and essentially absent from normal melanocytes and most of the malignant cells. The antigen binds specifically to the monoclonal antibody (XMEL) 12f3.2 and has an apparent molecular weight of about 170 KDal in the PSM cell line. Once antibodies are available which are specific for the epitope, the antibody can be used for screening for different antibodies from the same or a different host which bind to the same epitope by employing the subject antibody 12f3.2 or antibodies prepared to the epitope which cross-react with 12f3.2. Monoclonal antibody 12f3.2 is secreted by hybridoma cell line 12f3.2 and is described in U.S. Pat. No. 5,605,831.

The antibodies find use in diagnosis, with tissue employing cytology, with lysates of tissue or in detecting the subject epitope in blood or serum. A wide variety of techniques and protocols exist for detecting an antigen in a sample suspected of containing the antigen. Conveniently, the presence of the epitope can be determined immunologically by applying conventional immunoassays or histochemical staining techniques using antibodies reactive with the epitope expressed on the cell surface and/or shed into the blood. Protocols involve a wide variety of labels, which labels include radio-nuclids, enzymes, fluorescers, fluorescer-quencher combinations, chemiluminescers, magnetic particles, radiopaque dyes, and the like. These labels can be directly conjugated to the monoclonal antibody through a variety of covalently bonded linking groups and functionalities. Some of the techniques involve having one of the members of the antigen-antibody complex bound to a support, such as a particle or vessel wall, while other of the assays are performed in solution without a separation step. In a number of assays, the antibody need not be labeled, such as in a hemagglutination assay, or where anti-immunoglobulin is employed and the anti-immunoglobulin is labeled, so as to provide for indirect labeling of the subject monoclonal antibody. Assays which can be employed includes assays such as ELISA, RIA, EIA, FIA (Frye, et al., Oncogene 4:1153–1157, 1987) and the like.

Often, a sample is pretreated in some manner prior to performing a screening assay, generally immunoassay. A wide variety of immunological assay methods are available for determining the formation of specific antibody antigen complexes. Numerous competitive and non-competitive protein binding assays have been described in the scientific and patent literature and a large number of such assays are commercially available. It is well within the skill of one skilled in the art to perform such screening. Sample preparation will vary depending on the source of the biological sample. Cell or tumors and other tissue samples may be prepared by lysing the cells. Serum samples typically can be prepared by clotting whole blood and isolating the supernatant in accordance with well known methods.

For diagnosis of melanoma, PIN or prostatic carcinoma, biopsy specimens are the most likely source of samples for analysis. Conventional immunohistochemical staining techniques also can be used for detecting the epitope in tissue samples. For example, the tissue sample may be fixed in formalin or other standard histological preservatives, dehydrated and embedded in paraffin as is routine in any hospital pathology laboratory. When paraffin embedded preparations are used, the antigen should be evaluated to determine whether the preparation denatures the antigen for analysis. Sections are cut from the paraffin embedded material and mounted on glass slides or the sections are prepared from cryo-preserved tissue. Alternatively, cytological preparations can be used. For example, cells from the tissue sample can be fixed on a slide, typically by exposure to formalin in a buffer at physiologic pH, followed by suspension in acetone and pelleting onto gelatin-coated slides by centrifugation. The cellular antigen can be localized, either by exposure to labeled antibody or by exposure to unlabeled antibody and a labeled secondary antibody. The amount of the cell surface protein or antigen in the sample is directly proportional to the amount of bound label.

Biological fluids such as semen, serum, urine, saliva and sweat also may be assayed for the presence of the epitope as a way of monitoring for the presence or recurrence of a melanoma or prostatic tumor, particularly metastatic cancers. Whole body imaging techniques employing radioisotope labels can be used for locating melanomas, or prostatic carcinoma, both primary tumors and tumors which have metastasized. The antibodies of the present invention, or fragments thereof having the same epitope specificity, are bound to a suitable radioisotope, typically technetium-99, $^{123}$iodine, $^{125}$iodine, or $^{131}$iodine, or a combination thereof, and administered parenterally. For prostatic cancer, administration preferably is intravenous. High specific activity labelling of antibodies or fragments with technetium-99m is described for example in U.S. Pat. No. 5,317,091, U.S. Pat. No. 4,478,815, U.S. Pat. No. 4,478,818, U.S. Pat. No. 4,472,371, USRe 32,417, and U.S. Pat. No. 4,311,688. The bio-distribution of the label is monitored by scintigraphy, and accumulations of the label are related to the presence of melanoma cells or prostate cancer cells. Whole body imaging techniques are described in U.S. Pat. Nos. 4,036,945 and 4,311,688. The disclosures of the cited patents are incorporated herein by reference. Other examples of agents useful for diagnosis and therapeutic use which can be coupled to antibodies and antibody fragments include metallothionein and fragments (see, U.S. Pat. No. 4,732,864). These agents are useful in diagnosis staging and visualization of melanoma and prostatic cancer so that surgical and/or radiation treatment protocols can be used more efficiently.

Monoclonal antibodies can be used in other ways than binding to the subject epitopic site. Monoclonal antibodies to the epitopic site may in turn be used as antigens for the production of monoclonal antibodies specific for the idiotypic side of the monoclonal antibody to the cell surface receptor, for example 12f3.2. The anti-idiotypic monoclonal antibody can be used to detect the presence of antibodies in a host to the cell surface receptor, where the monoclonal antibody to the cell surface receptor and the physiological fluid to be diagnosed are from the same host. For example, where the monoclonal antibody to the cell surface receptor is a human antibody or a humanized antibody, then the monoclonal antibody to the cell surface receptor can be used as an antigen to make monoclonal antibody specific for the human idiotype for the cell surface receptor, which monoclonal antibodies can be used to detect antibodies to the cell surface receptor which are present in a human physiological fluid, for example blood or serum. The anti-idiotypic monoclonal antibody can be made in any host, for example rodent, more particularly rat or mouse.

In addition, the conformation of the idiotype of the anti-idiotypic monoclonal antibody resembles the epitope of the cell surface receptor and thus can serve as an antigen in competition with the cell surface receptor epitope. To that extent, the idiotypic monoclonal antibody can serve as a vaccine in inducing an immune response to the cell surface receptor epitope different from the immune response obtained with the cell surface receptor. Furthermore, the anti-idiotypic monoclonal antibody can serve as a reagent as a ligand which is competitive with the cell surface receptor. The monoclonal antibodies also can be used as a means of purifying the cell surface receptor from melanoma cells and prostatic cancer cells, for example in combination with a solid support, to form an affinity matrix.

The specificity of the monoclonal antibodies makes them useful as targeting agents for human melanoma cells or prostatic cancer cells. For example, the antibody can be coupled to a cytotoxic agent using methods known to those skilled in the art. For example, see U.S. Pat. No. 4,590,071 and U.S. Pat. No. 5,055,291, which disclosures are incorporated herein by reference. T-cell therapy also may be used, for example, see Rosenberg, *New England Journal of Medicine* 316: 789, 1987, which disclosure is incorporated herein by reference.

A composition of the invention for use in vivo generally will contain a pharmaceutically acceptable carrier. By this is intended either solid or liquid material, which can be inorganic or organic and be of synthetic or natural origin, with which the active component of the composition is mixed or formulated to facilitate administration to a recipient. Any other materials customarily employed in formulating pharmaceuticals are suitable.

The subject compositions can be provided as kits. The kits include an antibody or an antibody fragment which binds specifically to an epitope on melanoma or prostatic tumor cells, particularly an antibody produced by hybridoma cell line 12f3.2, and means for detecting binding of the antibody to its epitope on melanoma or prostatic tumor cells, either as concentrates (including lyophilized compositions), which may be further diluted prior to use or at the concentration of use, where the vials may include one or more dosages. Conveniently, where the kits are intended for in vivo use, single dosages may be provided in sterilized containers, having the desired amount and concentration of agents. Where the containers provide the formulation for direct use, usually there will be no need for other reagents for use with the method, as for example, where the kit contains a radiolabelled antibody preparation for in vivo imaging and/or diagnosis.

The following examples are offered by way of illustration and not by way of limitation.

EXAMPLES

Example 1

Preparation of Melanoma-Specific Antigen

The Xiphophorus fish genome was screened with conserved oncogene probes to identify oncogene-related genes on the chromosome carrying the complex locus which encompasses genetic information for the formation and location of macromelanophores and melanoma permissiveness. To isolate the genes of the major loci, oncogene probes were used to identify restriction fragment polymorphisms (RFLPs) as markers for these loci. RFLPs were found for genes similar to the src and the erb-B genes (Vielkind and Dippel, *Canadian Journal of Genetics and Cytology,* Vol. 26: 607–614 (1984)). The latter gene appears to be closely linked to the sex-linked pigmentary locus and is considered to be a candidate gene for some of the information contained in this locus.

Using the erb-B oncogene probe, a genomic phage library was screened and several positive clones were isolated. The clones were characterized by restriction enzyme mapping, which yielded five clones that encompassed the same restriction fragments as those identified in genomic southern blots using the erb-B probe. Probes from these Xiphophorus clones were used to screen two cDNA libraries yielding twenty clones, one of which carried an insert corresponding to the RNA fragment detected in a Northern blot analysis of the RNA from the PSM cell line. Restriction mapping of this clone as well as partial sequencing revealed that the identified gene is probably identical to the published Xmrk gene (Wittbrodt et al., 1989, *Nature* 341:415–421).

Differential PCR analysis with total RNA from testis, ovary, liver, kidney, brain, eye, skin, skin areas with melanophores, and melanomas using mrk-specific primers revealed that mrk is preferentially expressed in tissue containing melanophores and is highly expressed in the melanomas. This and the fact that this gene is found only in fish that can produce the cells giving rise to melanoma make it a specific gene for melanomatosis pigment cell growth.

Comparisons of the mrk sequence were done with sequences contained in the latest available Genebank and EMBL Genebank computer programs and its deduced amino acid sequence showed that the putative protein belongs to the family of receptor-tyrosine kinases which include an extracellular domain, a transmembrane domain and a cytoplasmic tyrosine kinase domain; the protein is most closely related to the human epidermal growth factor receptor (FIG. 1) but contains unique sequences not present in the epidermal growth factor receptor. The cytoplasmic tyrosine kinase domains are highly conserved domains and the transmembrane domain is unlikely to be highly antigenic. Therefore, the extracellular domain was further evaluated to find a portion of that domain which is not found in other proteins such as the epidermal factor receptor protein and for which high antigenicity can be assumed.

Figure 1B:
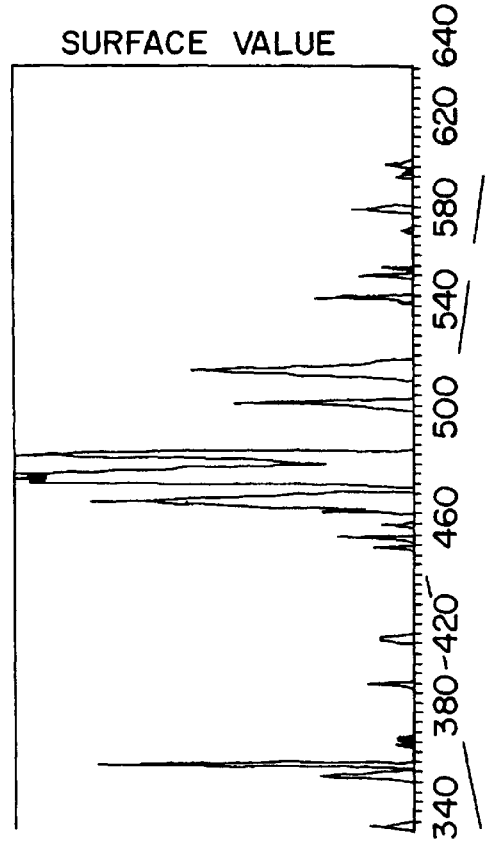
FIG. 1B shows surface values of amino acid residues 340–640 in which the peptide spans amino acids 480–489.
Figure 2A:
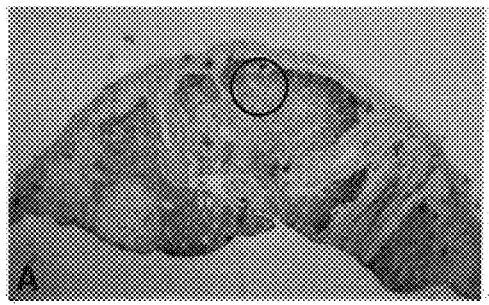
FIG. 2A: overview, 25×.
Figure 2B:
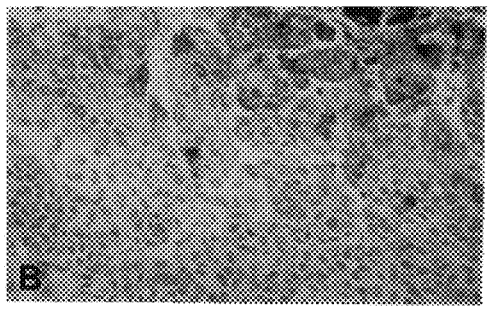
FIG. 2B: 250× of inset in FIG. 2A showing weak, diffuse red positive staining of nevocytic cells with occasional punctate staining.
Figure 2C:
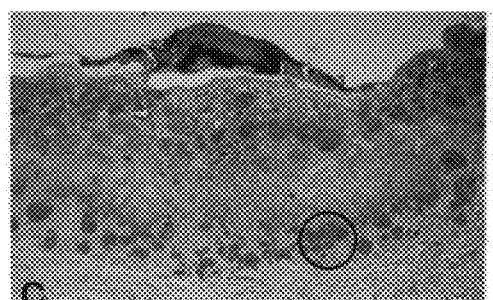
FIG. 2C: overview, 25×, strong red staining in upper and lower areas of primary melanoma, weaker staining in the more central area.
Figure 2D:
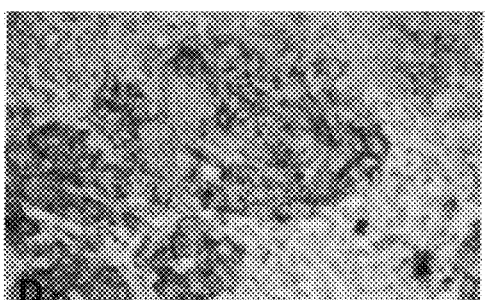
FIG. 2D: 250× of inset in FIG. 2C showing the strong, granular staining of nests of primary melanoma cells.
Figure 2E:
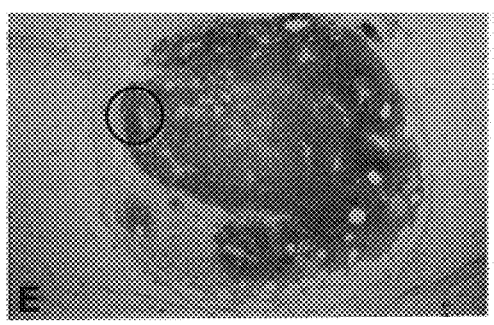
FIG. 2E: overview, 25×, staining appears to be stronger on the periphery than in the central part of the metastatic tumor.
Figure 2F:
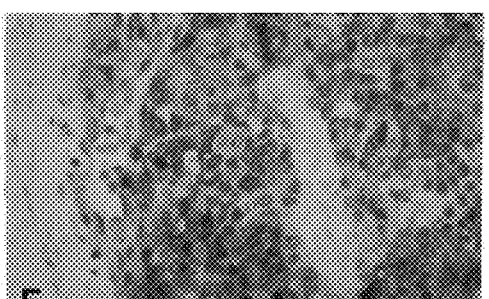
FIG. 2F: 250× of inset in FIG. 2E showing diffuse staining of variable intensity on melanoma cells.
Figure 2G:
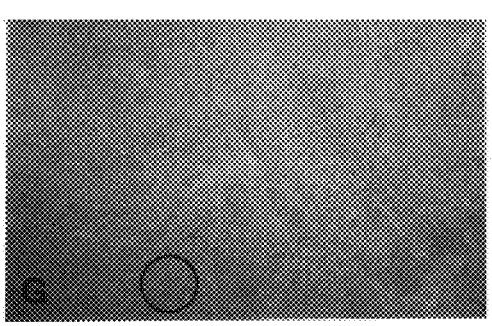
FIG. 2G: overview, 25×, showing areas of the metastatic melanoma with variable but weak staining.
Figure 2H:
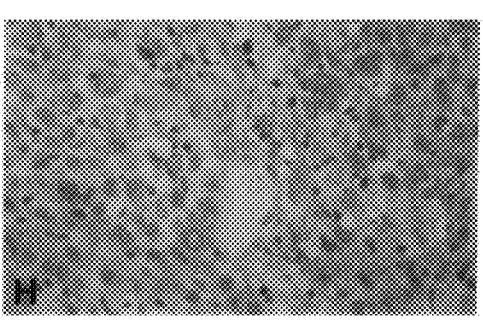
FIG. 2H: 250× of inset in FIG. 2G showing the weak diffuse and variable staining of the melanoma cells, occasionally a punctate staining can be seen. In all the sections from the various specimens no staining was observed on other cells including normal melanocytes. Immunostaining was performed with ABC peroxidase staining kit (Vector Lab.) and AEC (3-amino-9-ethylcarbazole, Sigma) as the chromogenic substance; sections were counterstained with Mayer's hematoxylin.
Figure 3:
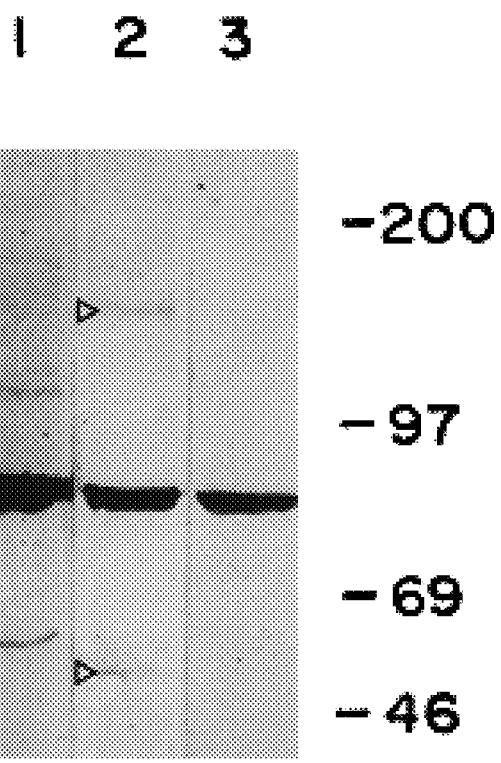
FIG. 3 shows a western blot analysis of proteins from cells of Xiphophorus PSM (lane 1,3) and human KZ13 melanoma cell line (lane 2). Proteins in lanes 1 and 2 were immunostained with XMEL hybridoma supernatant, rabbit anti-rat IgG(H+L) secondary antibody (Sigma) and DAB (3,3'-diaminobenzidine, Sigma) as chromogenic substance; proteins in lane 3 were reacted with hybridoma growth medium instead of XMEL supernatant. The XMEL monoclonal antibody stained faintly protein bands of 170,000, 115,000 and 60,000$M_r$ (closed triangles) in lysates from the PSM cells (lane 1) and stained faintly protein bands of 150,000 and 50,000$M_r$ (open triangles) in lysates from the KZ13 human melanoma cell line (lane 2). The strong protein band which appears in all 3 lanes most likely represents cross-reactivity with the growth medium and/or secondary antibody as it also appears in proteins from the PSM cells when the XMEL supernatant is replaced with the growth medium in the immunostaining reaction (lane 3). Numbers on the right side represent $M_r \times 10^3$ of rainbow protein marker (Bio Rad).
Figure 4A:
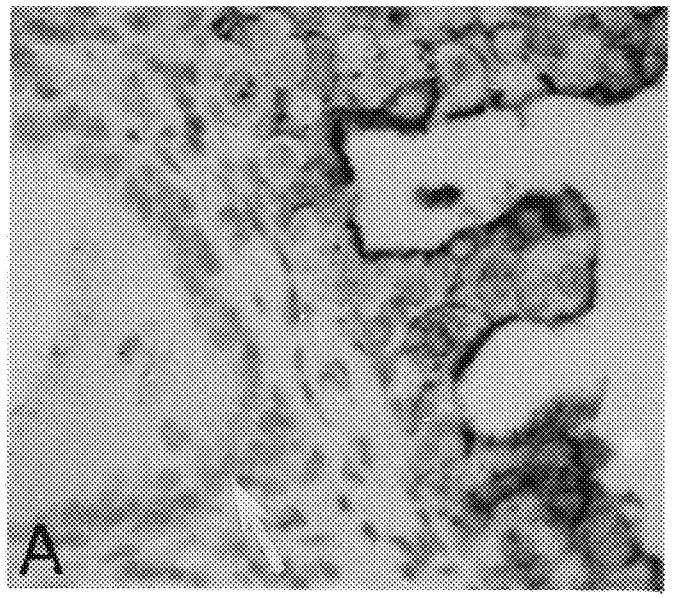
FIG. 4A shows that a high grade PIN reacts strongly with the XMEL MoAb, while the benign gland (arrow) is negative, as is the surrounding stromal component. Microscopically, this area of PIN demonstrates typical dysplastic features: enlarged nuclei, prominent nucleoli and increased number of cells.
Figure 4B:
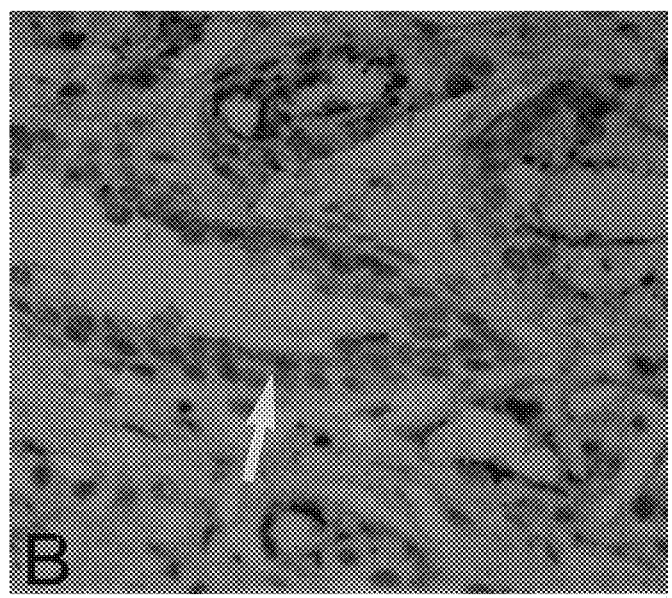
FIG. 4B shows prostatic cancer cells infiltrating around a normal gland (arrow).
Figure 4C:
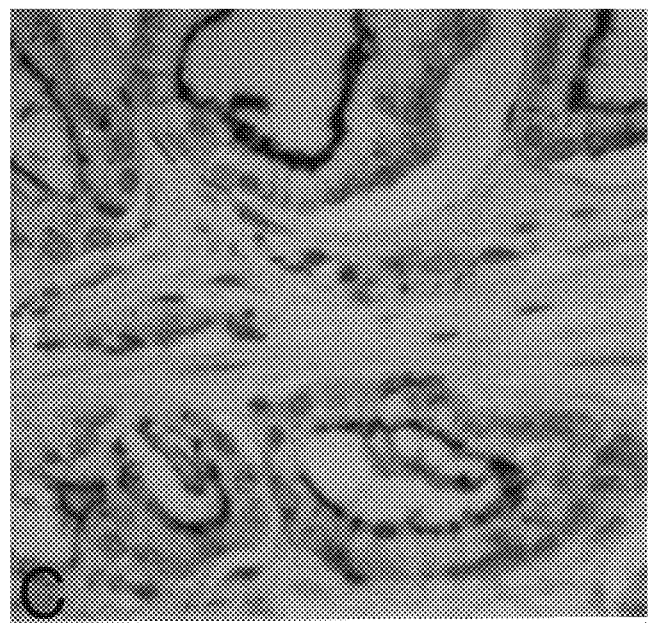
FIG. 4C shows positive staining of prostate cancer cells on membranes.
Figure 4D:
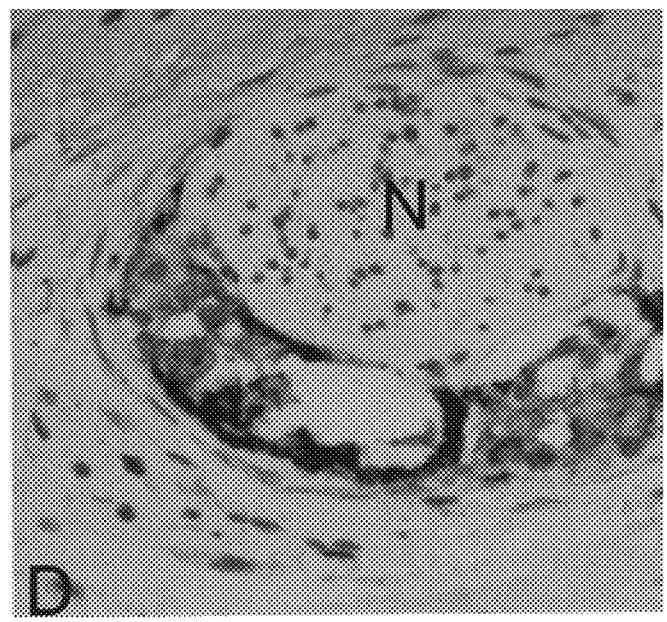
FIG. 4D shows typical invasion around a nerve (N) by a prostate cancer positive for XMEL MoAb binding.

A computer modeling (Surfaceplot-Synthetic Peptides, Inc.; see Parker et al., *Biochem* 25:5426–5432, 1985) of the putative mrk-receptor protein was done to predict the antigenicity of portions of this protein. An exposed sequence of 10 amino acids (L-F-R-S-E-D-Q-S-I-E) (SEQ ID NO:1) of the extracellular domain met this demand. The amino acid sequence of this portion of the mrk-protein also avoids any similarity to the amino acid sequences of the true epidermal growth factor receptor of fish or human origin and according to an extensive search in the gene/protein data banks, no significantly similar amino acid sequences exist in other proteins. This sequence, therefore, appears to be rather specific for the novel receptor; a peptide was therefore synthesized and used for the generation of antibodies (FIG. 1). For coupling to the hapten, the peptide was synthesized with a cysteine residue at the N-terminus. The peptide was coupled to the hapten KLH (keyhole limpet hemocyanin, Pierce Chemical Co.), via SMCC (succinlmidyl 4-(N-malemido-methyl)cyclohexane-1 carboxylate, Pierce Chemical Co.) (see Sutcliffe et al., 1980; Sela, Synthetic Vaccines Vol. 1 R. Amon (Ed.), CRC Press, Boca Raton, Fla., pp. 85–92, 1987).

Example 2

Preparation of Antibodies to Mrk-receptor Protein Fragment Immunization

The hapten-peptide conjugate was mixed 1:1 with Freund's complete adjuvant and 0.8 ml injected intraperitoneally (ip) into each of three Fischer rats (125–150 g body weight) at a concentration of 0.5 mg/ml. After 14 days, a second ip injection of the KLH-peptide conjugate was given, and then 4 times at 14 day intervals the uncoupled peptide at a concentration of 0.5 mg/ml was injected. At that time, a positive immunoresponse of the serum of the rats was identified by standard ELISA methodology using cells from the Xiphophorus fish melanoma cell line (PSM line) which show a high expression of the mrk gene as positive and the Xiphophorus fibroblastoid cell line (XGI line) as negative control as was the rat preimmune serum; staining was done using goat anti-rat IgG (H+L) (Jackson Immun. Lab.) as secondary antibody conjugated to horseradish peroxidase, and OPD (o-phenylenediamine dihydrochloride, Sigma) as the chromogenic substrate. Another ip immunization with the peptide at a higher concentration (0.8 mg/ml) then was done followed by an intravenous injection of the peptide (0.8 mg/ml) without Freund's adjuvant 3 weeks later. Four days later monoclonal antibody production was started by fusing $4 \times 10^8$ spleenocytes from the rat which gave the strongest immunoresponse to $0.8 \times 10^8$ SP2/O mouse myeloma cells. Fourteen 96-well microtitre plates were seeded with a spleen cell density of $1.25 \times 10^3$ cells/well. Cells were grown for 7 days in HAT-DMEM (TFL Media Preparation Service, Vancouver, B.C.) supplemented with 50 µl/ml of Interleukin-8.

Isolation of Clones

Screening of monoclonal producing hybridoma cells was done on terazaki plates coated with cells fixed in 0.05% glutaraldehyde from the PSM melanoma cell line as positive control and as negative controls with cells from the XGI cell line, from a gonadal cell line of trout, with fibroblasts and bone marrow cells from human; staining was done as noted above. Cells from 28 wells which yielded a positive signal with the PSM cells were transferred from the microtitre plates into 1 ml of HT-DMEM in 24-well plates and after 3–6 days plated in methylcellulose. Isolation of individual pure hybridoma clones was done by picking at least 12 individual colonies derived from the original positive cells, transferring them into 96-well microliter plates and testing again for positive reactivity with the PSM cells and also with the peptide; as negative controls the cells mentioned above were also tested. Three clones were isolated which produced monoclonal antibodies that reacted positively with the peptide and the fish melanoma cell line but exhibited no reactivity with the other cells.

Two other clones, 10A3 and 3B7 reacted less strongly and three clones, 5C1, 6E4, and 14C7, reacted not only with the peptide and the fish melanoma cell line but also with a trout cell line, making them more general.

Typing of Antibody

Supernatants of the three positive hybridoma clones were subsequently reacted with cultured PSM as well as XGI cells fixed on the culture dishes with 4% paraformaldehyde (20 min, RT); staining was done using anti-rat IgG(H+L) conjugated to horseradish peroxidase (Jackson Immun. Lab.) and DAB (3,3'-diaminobenzidine, Sigma) as chromogenic substrate or with goat anti-rat F(ab)'$_2$ FITC-coupled secondary Ab (Cappel Lab.). The clone 12f3.2 produced the strongest signal with the PSM cells and we thus concentrated on it first. Typing of this mAb using a Bio-Rad kit which is a mouse typing kit but also has cross-reactivity with rat antibodies revealed that the monoclonal antibody 12f3.2 is an IgM(k).

Immunostaining of Cells from Xiphophorus PSM Melanoma Cell Line

To further verify the specificity and also identify the location of the antigen recognized by the peptide-specific mAb, cultured cells of the PSM cell line were fixed and stained (see above) with supernatants of the mAb producing clone 12f3.2. The PSM line contains all stages of pigment cell differentiations; spindle-shaped premelanocytes, young melanocytes with fine few dendrites, polydendritic adult melanocytes, and finally also the large melanophores with broad dendrites which are fully loaded with brown-black melanin pigment. Staining however, was found only in the younger stages, the melanocytes, at the contact sites of their dendrites, on the edges concentrated in spots and in areas where the cells narrow towards the dendrites. This staining pattern is typical for a cell surface receptor or cell contact type antigen. This is in keeping with data we have deduced from the nucleotide sequence, i.e. that the putative mrk protein is a cell surface receptor. This staining behavior is more prominent in vitally stained cells and using the FITC anti-rat IgG conjugate.

Example 3

Characterization of Antibody Specificity for Melanoma Tissue mAb Reacts with Pigment Cells from Normal and Melanoma Tissue in Xiphophorus While the culturing of melanoma cells can yield valuable information, the classification of the disease state must be done on sectioned material. In order to test the suitability of the produced mAb 12f3.2, cross-sections from frozen as well as paraffin embedded material were stained using the avidin-biotin procedure (ABC staining kit, Vector Lab.) and AEC (3-amino-9-ethylcarbazole, Sigma) as chromogenic substrate. So far we have obtained with mAb 12f3.2 supernatant (1/50 in PBS) a positive signal in frozen positioned and acetone-fixed Xiphophorus dorsal fin material which contains in the dermis fully differentiated melanophores and immature, non-pigmented precursors underlying the differentiated cells. Interestingly, staining was not observed in the melanophores but in the precursors. Sections of melanoma tissue stained positive in areas representing tumor growth and in areas which are composed of spindle-shaped, lightly pigmented cells.

mAb Stains Human Melanoma Cells But Not Normal Melanocytes In Vitro

The encouraging results of the detection of melanoma cells from our model led us to further test the mAb by immunostaining human melanoma cell lines derived from patients from whom B-cells were also available as a control. The cells in the culture dishes were fixed with 0.4% paraformaldehyde for 30 min. at RT and then immunostained as described above for cultured fish cells. All three melanoma cell lines KZ-2,-13,-28 stained positively but each in a characteristic way. The spindle-shaped, dendritic KZ-2 cells exhibited an evenly distributed staining with some spots of more concentrated staining, the dendritic to polydendritic KZ-13 cells exhibited the staining in the cell's body and at the start of the dendrite, and the larger KZ-26 cells which have broad dendrites and tend to conglomerate show strong staining in the centers of these concentrations presumably where their dendrites contact each other. The B-cells of the patients did not show any staining at all nor did the cultured melanocytes derived from human foreskin. The history of the human melanoma cells are not quite clear with regard to classification of the described stages above, i.e. radial, vertical growth phase, metastatic phase. However, the KZ-2 cells show the fastest, KZ-13 slower and the KZ-26 cells an even slower growth. Thus, the mAb appears to yield a characteristic staining of melanoma cells of various growth potentials.

mAb Reacts with Human Melanoma Tissue

The most important question to answer was whether or not the mAb specifically recognizes human melanoma tissue. Sections from three primary and four metastatic acetone-fixed and paraffin-embedded human melanoma specimens obtained from six different patients were stained with the mAb 12f3.2 supernatant diluted 1/50 with PBS as described above for the sections of fish tissue; all melanomas showed positive staining. In the primary melanomas, nests of stained (positive) melanoma cells were observed while in the metastatic tumors the positive cells were more dispersed; two of the metastatic tumors of the same patient showed strong staining that appeared as grainy spot indicative of antigen located on the surface of the melanoma cells. The healthy skin, including melanocytes and other cell types within the melanoma, e.g. lymphocytes, did not show any staining.

Identification of Melanoma Related Characteristics by Western Blotting

Another possibility to identify melanoma specificity is to analyze electrophoretically separated proteins on nitrocellulose blots. Therefore cells of the PSM and KZ melanoma cell lines were lysed and separated and blotted according to standard conditions and the blots immunostained with the mAb. Only the melanoma showed a positive signal; the PSM cells revealed a weak signal at 170 KD which would be expected from the predicted amino acid sequence and a strong signal of approx. 70 KD which may be a degradation product of the activation and signal transduction of the mrk-receptor tyrosine kinase (see Ullrich and Schlessinger, Cell 61:203–212, 1990). Signals in very similar size ranges were detected in the human melanoma cells. No signal at all was found in lysates derived from the control XGI cell line, which is to be expected as these cells do not express the mrk gene.

A rat monoclonal antibody was produced against a synthetic peptide which represents a putative highly antigenic portion of a novel receptor tyrosine kinase protein. The protein is coded by a melanoma pigment cell specific gene which was cloned from Xiphophorus fish. Xiphophorus represents an animal melanoma model which is well established as a model for human melanoma formation.

The mAb recognizes the prepigment cells in situ, the undifferentiated melanocytes of a Xiphophorus melanoma cell line and also the melanoma cells in growth areas of Xiphophorus melanomas. It also reacts characteristically with cultured human melanoma cells of different growth potentials and with primary and metastatic secondary melanomas in situ. The staining pattern of secondary melanoma cells has a grainy appearance. The mAb does not react with normal human cultured melanocytes nor with those that are located in the normal skin adjacent to the melanomas. In conclusion, the mAb can be used as a tool for histochemical characterization of melanoma cells in patients for immunodiagnosis of both primary and metastic melanomas, and for treatment of melanomas by immunotherapy.

Example 4

Antibody 12f3.2 Reactivity in Human Melanomas

To test the antibody 12f3.2 (XMEL) reactivity in human melanoma and to answer the question whether the XMEL antigen is related to the early or later stages of melanoma progression, 136 specimens covering the stages of progression of malignant melanoma were immunostained according to the protocols in Example 3. XMEL reactivity can be summarized as follows: (1) weak reactivity was found in 2/18 (18%) common acquired nevi, (2) strong XMEL staining was observed in 8/21 (38%) dysplastic nevi which is believed to be the precursor of malignant melanoma, (3) similarly strong reactivity was seen in 53/60 (88%) primary melanomas and (4) staining was less consistent in metastatic melanomas ranging from very strong to weak and absent in some of them, 23/37 (62%) were XMEL positive. These data suggest that the antibody recognizes an antigen that is related to the early events (primary melanomas) rather than the later stages of progression to the metastatic phenotype (metastatic melanomas). In another cohort study of high risk patients with deep melanomas, XMEL immunoreactivity was found not related to patient outcome while Breslow's depth of invasiveness was (Breslow's depth is considered to be the most reliable, single prognosticator but is not always applicable). The findings also indicate that XMEL antibody recognizes early stage rather than late stage of melanoma.

The reactivity of XMEL with the different progression stages is completely different from that of antibodies against the EGFR (epidermal growth factor receptor) protein. The resultings of antibodies against EGFR protein show an increase in reactivity with an increase in progression and the highest reactivity is found in metastatic melanomas; whereas the results of XMEL antibody show the highest reactivity with primary melanomas. Therefore, the XMEL antibody does not recognize only the EGFR protein.

Example 5

Specificity of XMEL Antibody

This study was performed to determine the specificity of the XMEL antibody. A screen of nearly 100 non-melanocytic malignancy samples were tested by immunostaining as described in Example 3. There was virtually no cross reactivity with any other cancer type; XMEL immunostaining was observed on all 4 carcinomas of the prostate. Fourteen more samples were studied. All specimens exhibited strong XMEL reactivity on the membranes of cells representing high grade PIN, especially on cells at the edges of invasive carcinoma in PIN and in cancerous glands in the vicinity of PIN. These are sites presumed to be characteristic of cells which have changed into invasive malignant cells.

Example 6

Specificity of Antibody 12f3.2 for Prostate Cancer

The initial study was performed on biopsies from radical prostatectomies (15 cases), all these cases fulfilled the criterion that no treatment prior to the operation was given to the patient which could otherwise cause XMEL antibody reactivity. In the studies, it was observed that the XMEL antibody reacted with high grade prostatic intraepithelial neoplasia (hg PIN) and invasive prostatic cancer cells; hg PIN is considered to represent the precursor of the malignant prostate cancer cell. We then extended these studies to further 34 cases of radical prostatectomies and normal tissue samples (Table 1 and 2).

TABLE 1

Immunohistochemical reactivity of the monoclonal antibody XMEL from the hybridoma clone 12f3.2 in biopsies from radical prostatectomies and samples from normal tissues A. Prostatectomies

| Biopsy from patient | % of XMEL positive cancer cells | XMEL staining intensity on cancer cells | XMEL staining in normal gland | Control |
|---|---|---|---|---|
| A-1 | 100 | 3+–4+ | — | — |
| A-2 | 2 | 1+–2+ | — | — |
| A-3 | 60 | 3+–4+ | — | — |
| A-4 | 60 | 3+–4+ | — | — |
| A-5 | 50 | 3+–4+ | — | — |
| A-6 | 95 | 4+ | — | — |
| A-7 | 70 | 3+ | — | — |
| A-8 | 2 | 1+ | — | — |
| A-9 | 2 | 2+ | — | — |
| A-10 | 2 | 2+–3+ | — | — |
| A-11 | 40 | 2+–3+ | — | — |
| A-12 | 5 | 1+ | — | — |

In these biopsies, high grade prostatic intraepithelial neoplasia (hg PIN) was not observed.

B. Normal tissue

| Sample # | Tissue Type | Control |
|---|---|---|
| A-13 | normal prostate | — |
| A-14 | seminal vesicle | — |
| A-15 | liver | — |
| A-16 | muscle | — |
| A-17 | kidney | — |
| A-18 | lung | — |

-continued

| Sample # | Tissue Type | Control |
|---|---|---|
| A-19 | colon | — |
| A-20 | skin | — |

XMEL staining is marked as: −=absent and +=present; intensity of positive staining was graded as: 1+=weak; 2+=moderate; 3+=strong; 4+=very strong; controls were done for all cancer and normal tissue samples by replacing the primary XMEL antibody with either an unspecific rat antibody or by hybridoma growth medium and did not exhibit any staining.

TABLE 2

Immunohistochemical reactivity of the monoclonal antibody XMEL from the hybridoma clone 12f3.2 in biopsies from the radical prostatectomies from a cohort of cancer patients.

| Biopsy from patient | % of XMEL positive cancer cells | XMEL staining intensity on cancer cells | XMEL staining intensity on cells in hg PIN, if present | XMEL staining in normal gland | Control |
|---|---|---|---|---|---|
| B-1  | 0 |    |    | — | — |
| B-2  | 0 |    |    | — | — |
| B-3  | 10 | 1+ |    | — | — |
| B-4  | 0 |    | 1+ | — | — |
| B-5  | 0 |    | 1+ | — | — |
| B-6  | 0 |    |    | — | — |
| B-7  | no cancer |    | 1+ | — | — |
| B-8  | 0 |    |    | — | — |
| B-9  | 0 |    |    | — | — |
| B-10 | 10 | 1+ |    | — | — |
| B-11 | 0 |    |    | — | — |
| B-12 | 0 |    | 1+ | — | — |
| B-13 | 0 |    | 1+ | — | — |
| B-14 | 0 |    |    | — | — |
| C-1  | 0 |    | 1+ | — | — |
| D-1  | 30 | 1+ |    | — | — |
| D-2  | 10 | 1+ | 1+ | 1+ | — |
| D-3  | 20 | 1+ | 1+ | — | — |
| D-4  | 30 | 1+ | 1+ | — | — |
| D-5  | 40 | 1+ | 3+ | — | — |
| D-6  | 5  | 1+ | 1+ | — | — |
| D-7  | 0 |    |    | — | — |

XMEL staining is marked as: −=absent and +=present; intensity of positive staining was graded as: 1+=weak; 2+=moderate; 3+=strong; 4+=very strong; controls were done for all cancer and normal tissue samples by replacing the primary XMEL antibody with either an unspecific rat antibody or by hybridoma growth medium and did not exhibit any staining.

In Table 1B, we presented results from normal tissue samples, because for a possible immunotherapy with this antibody it is necessary to establish that the antibody shows no cross-reactivity with normal tissues of the patient. As can be seen from Table 1, all prostate cancers stained positive with the antibody although with various intensities and variable numbers of the cancer cells, while the normal gland component was negative as were the normal tissues including the sections from non-cancerous, normal prostate.

The data shown in Table 2 pertain also to the question of specificity but represent the initial data on the question of prognosis. These samples were chosen from a cohort of patients from whom tissue blocks had been obtained and stored for several years. The reactivity with these biopsies is less strong, which most likely is due to the fact that these are sections from old paraffin blocks which usually yield a less strong immunosignal. The fact that 14/22 cancer and/or PIN samples stained positive shows that the antibody is specific for the malignant stages of carcinoma of the prostate.

Example 7

Immunoreactivity in Prostatic Carcinomas

A total of 115 biopsies from prostatectomies (Studies 1–4) and 10 biopsies from normal glands (Study 5) were tested in the experiment using immunostaining as described in Example 3. The specimens used in studies 1–3 are cancer of the prostate. The specimens of study 4 are negative for cancer of the prostate. Each biopsy specimen was taken from a different individual. 91/94 (97%) of carcinoma of the prostate and 52/54 (97%) of high grade PIN reacted positively with the XMEL antibody. The data are summarized in Table 3.

TABLE 3

Immunohistochemical reactivity of the monoclonal antibody XMEL in biopsies from radical prostatectomies and normal glands

| Study | # of biopsies | # of XMEL positive staining | XMEL staining intensity on cancer cells | # of biopsies having hg PIN | # of XMEL positive staining in hg PIN | XMEL staining intensity on cells in hg PIN, if present |
|---|---|---|---|---|---|---|
| 1 | 14 | 14 | 3+–4+ | 14 | 14 | 3+–4+ |
| 2 | 12 | 12 | 3+–4+ | 0 |    |    |
| 3 | 68 | 65 | 2/3+–4+ | 37 | 35 | 3+ |
| 4 | 21 | 0 |    | 3 | 3 | 2+–3+ |
| 5 | 10 | 0 |    | 0 |    |    |

Intensity of positive XMEL staining was graded as: 1+ = weak; 2+ = moderate; 3+ = strong; 4+ = very strong;
hg PIN = high grade prostatic intraepithelial neoplasia.

Intensity of positive XMEL staining was graded as: 1+weak; 2+=moderate; 3+=strong; 4+=very strong;
hg PIN=high grade prostatic intraepithelial neoplasia.

The high incidence of XMEL antibody staining of PIN and prostate cancer suggests that the antigen and its encoding gene are instrumental in the development of prostate cancer.

Example 8

XMEL Immunostaining of Prostate Carcinoma

To test the reactivity of the XMEL antibody on prostate carcinoma, immunostaining of sections from paraffin-embedded prostatectomies with XMEL antibody and biotin-streptavidin-peroxidase detection system was performed using AEC as a chromogenic substrate as described in Example 3. XMEL antibody detected surface antigen on high grade PIN and invasive malignant cells. The results are shown in FIG. 4. FIG. 4 also shows that the best XMEL staining was found on moderately differentiated carcinoma cells (Gleason grade 3) and that less immunostaining was found on only differentiated cells. Thus XMEL reactivity may aid in distinguishing high and low risk cancers. No reactivity was observed in the stromal component nor on the normal acini. Some membrane luminal staining was observed, indicating that XMEL-reactive cell surface antigen is shed into the blood of prostate cancer patients.

Example 9

XMEL Reactivity in Relation to Cancer Diagnostic/Prognostic Parameters

The almost 100% reactivity of XMEL with high grade PIN and prostatic cancer cells (see Example 7) strongly suggests a role for the XMEL antigen in prostatic cancer particularly in the early stages. To determine if XMEL reactivity is an indicator for the disease stage, 277 samples for which a pathological report containing information on tumor stage, PSA level, Gleason grade, follow up, and other demographic information is available are obtained. Included in this cohort are 100 cases with needle biopsy results which allows the comparison of XMEL reactivity with the diagnosis of the physician/pathologist and the cancer that ultimately occurs. To determine whether the XMEL antigen is expressed in clinically insignificant small volume cancers, 40 specimens with occult prostatic carcinoma from radical cystoprostatectomy of bladder cancer are evaluated. As controls, benign prostatic hyperplasia and PIN of lower grades from the tissue bank are included. Strong staining in the high grade PIN and the invasive cancer cells are expected and the relationship between XMEL reactivity and the usual pathological/clinical parameters is determined.

Sections are prepared from these samples and immunostained as described previously. XMEL reactivity is determined by two individuals in a blind study by assessing both intensity of staining and percentage of positively stained cells. Intensity of staining is scored as follows: −absent=1, +weak=2, ++moderate=3, +++strong=4; percentage of positive cells will be graded according to the following: 1–5%= 1, 6–25%=2, 26–50%=3, 51–75%=4, and 76–100%=5. Strength of reactivity is defined as intensity times percent of positive cells and intensity score over the normal and malignant glands. The results is assessed using analysis of variance statistics (ANOVA). Following update of patient status, the XMEL data along with the pathologic/clinical data is analyzed using a Cox proportional hazards model to evaluate whether the level of XMEL activity is a significant diagnostic/prognostic factor for the evaluation of the cancer.

Example 10

Determination of the Presence of a 170 KDa XMEL Reactive Product in Sera from Patients with Confirmed Prostatic Carcinoma Sera from 120 patients with localized prostate cancer are collected. These samples are drawn before surgery and 3 months post-radical prostatectomy for determination of prostate specific antigen (PSA) levels and will be used by us for western blot analysis. Pre- and post-operative levels are evaluated with pathologic stage, grade and PSA levels. To evaluate cancer specificity, serum samples from young men with normal DRE and PSA levels (i.e. low risk for prostate cancer) are measured for presence of 170 KDa XMEL-positive product as well.

In the study, the XMEL antibody is used in form of serum-free hybridoma supernatant. Alternatively, the antibody can further be purified by affinity chromatography on an anti-k-column or a Con A-Sepharose column and fragmented by the Pierce Immuno-Pure Fragmentation kit. A purified antibody/fragment allows the performance of a capture ELISA for assessing the serum protein and increases signal strength in the assay. Statistical analysis is done as indicated above.

Example 11

Isolation of Human mrk Gene

The similarities of fish and human melanoma formation and the XMEL reactivity with both fish and human melanoma suggests that the XMEL antigen expressed in human melanoma is encoded by a gene homologous to the novel receptor tyrosine kinase detected in the fish model. However, XMEL also recognizes prostate cancer cells. While there is no obvious similarity between both cancers, a receptor kinase can be involved in the formation of more than one cancer. Thus, it is possible that the same antigen is expressed on both cancers or a different antigen sharing the same or different epitope with a different affinity to XMEL. Therefore, the XMEL antigen could be encoded by different genes not only between fish and humans but also between melanoma and prostate cancer. What is particularly striking is that XMEL appears to preferentially recognize a membrane-bound antigen on cells of the precursor and intermediate and less on cells of the advanced stages in both tumors, suggesting that the detected XMEL antigen is indicative of an early or even initiating event in tumor formation.

A common method to clone a gene from one species when the sequence from another species is known is to use degenerate primers in a PCR protocol. A dilemma arises in selecting primers—if selected conserved in all EGFR family genes (or to the kinase domain in the kinase superfamily) the primers may lose their specificity but if the selected sequences are not conserved in the EGFR family they are less likely also to be conserved in the human mrk gene (Hmrk). We reasoned the peptide sequence to induce the antibody would be reasonably conserved in the Xiphophorus and human mrk genes and designed degenerate primer(s) to this sequence.

In order to reduce the probability of spurious amplification but at the same time increase the probability of primer annealing and chain elongation of the proper template, the TD PCR (see Don R. H., Cox P. T., Wainright B. J., Baker K, and Mattick J. S. *Nuc. Aicd Res.* 19(14):4008, 1991 and Roux K. H. *Biotechniques* 16:812, 1994) using Xmrk primers that encode, at the 3' end at least, amino acids which are conserved in all human EGFR family genes are used. By ending the primers with a codon to a conserved amino acid, minus the wobble base, it can be ensured that there will be a perfect match at the 3' terminus. Furthermore, since the use of PCR is predicated on the tolerance of mismatches, other than at the 3' terminus, degenerate primers are not required. Preferential amplification of Hmrk over the EGFR family genes occurs since the Xmrk primers have the fewest mismatches to Hmrk.

Although expression of cDNAs from various organisms as bacterial fusion proteins has been widely used to identify genes encoding proteins to which antibodies are available, our efforts to immunoscreen bacterial cDNA expression libraries did not result in isolation of sequences that share homology with Xmrk sequences. Xmrk encodes a surface receptor which cannot adopt its native conformation in the bacterial cell and can lead to precipitation of the fusion protein making detection by the XMEL in the immunoscreen impossible. It therefore is preferable to use a mammalian expression system in which a receptor is presented in its native configuration on the cell surface. COS cells provide the most proven and efficient mammalian expression cloning system for cell surface proteins (Seed, 1987). This type of expression cloning has been optimized (Kay R. and Humphries R. K, *Methods in Molecular and Cellular Biology* 2:254–265, 1991) and applied (Kay R., Takei F, Humphries R. K *J. Immunolol.* 15:1952–1959, 1990). It has the advantage that high levels of expression are obtained alternatively, cell surface proteins can be cloned by retroviral transmission and expression of cDNA libraries. This approach results in stable expression of cDNAs allowing the repeated selection and expansion of rare cell clones expressing the targeted antigen. (Whitehead et al., *Mol. Cell Biol* 15:704–710, 1995).

Expression cloning in the COS cell system is performed as follows. A cDNA library from the LNCaP cell line is established in the expression vector pCTV85, which is a dual purpose expression vector that is equally effective for COS cell expression or as a retroviral vector. Pooled plasmid DNA for the library is electroporated into COS cells. After a 48–72 growth period, COS cells expressing the XMEL antigen on their surface are isolated with the XMEL antibody by panning. Replicated plasmids within the selected cells are cloned and re-purified. Several rounds of electroporation and selection of expressing COS cells are typically required to enrich for and finally isolate positive cDNA clones, identified by their ability to confer high levels of XMEL reactivity on COS cells.

A library is screened via retroviruses. The plasmid DNA of the library is transfected into the BOSC 23 ecotropic packaging cell line, and secreted virus is used to infect NIH 3T3 cells. After a 4 day period of expansion, the infected cells are viably sorted with the XMEL antibody, re-expanded in culture, resorted and then tested for XMEL reactivity by FACS. When a pure XMEL reactive population is obtained, the proviral library cDNAs carried by the cells are recovered by CPR, cloned into pCTC85, and tested for their abilities to confer XMEL reactivity as individual clones.

Using antibodies bound to various solid matrixes has been a general method to isolate antigens to high enough purity to be used in microsequencing of peptides. From these sequences degenerate oligonucleotides can be synthesized which allow first to clone parts of the gene from total RNA or cDNA libraries in a PCR approach and then the total cDNA of the gene. Sequencing of the cloned PCR products determines the encoded amino acid sequence and can be used to verify that the correct gene has been isolated.

The XMEL MoAb produced under serum-free conditions in hybridoma serum-free growth medium (Gibco) is covalently linked to CNBr-activated Sepharose beads (Pharmacia). Lysates from Nonidet P40 solubilized LNCaP cells are incubated with these beads. Bound proteins are eluted by boiling in 1% SDS, concentrated by ultrafiltration, further purified by size exclusion HPLC, if necessary, and then subjected to preparative SDS-PAGE (Damen et al., 1996). Following Ponceau S staining of transferred proteins on an Immobilon membrane, the protein band is excised and the amino acid sequence determined using methods known to those of skill in the art. The sequence is then compared with known sequences in databanks such as Genbank. If the amino acids are not in the data banks, degenerate oligonucleotides are generated and the cDNA for this protein is cloned and sequenced.

To determine whether or not the XMEL antibody might bind to a peptide sequence other than that used for the generation of the antibody, short peptides displayed by phage display libraries are surveyed for tight binding to various targets incubating antibodies, cell surface receptors or enzymes by incubating the phage library with the immobilized target, e.g. an antibody, washing away unbound phages and then eluting the target-bound phages. Alternatively, the phage library can be bound to the target insolution and this complex cpatured via an immobilized secondary antibody. This allows selection for tight and low binding epitopes to the target by simply varying the molar ration betwen phages and target. After 3–4 rounds an enriched pool is obtained and the amino acid epitope sequences of the displayed peptides in individual clones are determined by sequencing the corresponding coding sequence in the phage DNA.

We have used both methods in screening for tight binding epitopes to the XMEL anitbody using a phage 15 mer display library. Both methods led to the same small population of clones with a consensus sequence of DFPGL which is different from the XMEL peptide sequence LFRSEDQSIE (SEQ ID NO:3).

| melag 1 | NARVCDFPGISCVYR | (SEQ ID NO:4) | 16 clones |
| melag 2 | LSGSVPSLVAPYAPW | (SEQ ID NO:5) | 10 clones |
| melag 3 | RDLFSPCPFPGFCRQ | (SEQ ID NO:6) | 2 clones |
| melag 4 | MTGNSCGDFPAYCRL | (SEQ ID NO:7) | 6 clones |
| melag 5 | WPFVDEPGLIRLPAA | (SEQ ID NO:8) | 3 clones |
| melag 6 | RGGSCLALSSLALF | (SEQ ID NO:9) | 1 clone |
| melag 7 | GGFPGLMFGHICSD | (SEQ ID NO:10) | 1 clone |

One strongly XMEL positive gtl1 phage expression clone, gtl1-52, from a melonama cell line contained a small insert encoding only 44 amino acids that includes the consensus sequence.

The probes are used to isolate the entire transcript by screening a LNCaP cDNA library for overlapping clones and analyzed for differential expression on northern blots of RNA from the LNCaP cells in comparison to cells from the DU 145 prostate cancer cell line which is negative for XMEL reactvitiy. In situ hybridization is done (Human Genome FISH Mapping Resource Centre, HSC, Toronto) to determine the chromosomal location of the gene and if it is associated with a locus involved in frequent chromosomal aberrations in prostate cancer development. These and sequence data will confirm that we have a gene that contributes to the genesis of prostatic carcinoma. Possible oncogenic activation of the gene is then investigated. For example, if the human gene is similar to the Xmrk gene, i.e. a gene belonging to the growth factor receptor oncogene class, mutational, oncogenic activation could be of various sorts ranging from overexpression to partial deletion, insertion, rearrangement, point mutation. Gross changes are identified by RFLP analyses of DNAs from normal blood and matched carcinoma material and subtler changes by comparative sequence analysis of cDNA of normal and tumor origin.

The gene is then used to find other genes functionally associated with it (e.g. transactivators, the ligand, downstream effectors) in order to ascertain the biochemical pathways leading to prostatic carcinoma.

All publications including patent applications mentioned in this specification are indicative of the level of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be apparent to one of ordinary skill in the art that many changes in modifications can be made thereto without departing from the spirit or scope of the appended claims.

What is claimed is:

1. A method for detecting high grade prostate intraepithelial neoplasia in a human host, said method comprising:

combining a sample from said human host with antibodies or antibody fragments which bind specifically to a peptide having the amino acid sequence depicted in SEQ ID NO:1, and detecting formation of immune complexes as indicative of the presence of high grade prostate intraepithelial neoplasia.

2. A method for detection of prostate carcinoma in a human host, said method comprising:

combining a sample from said human host with antibodies or antibody fragments which bind specifically to a peptide having the amino acid sequence depicted in SEQ ID NO:1, and detecting formation of immune complexes as an early indication of the presence of prostate carcinoma.

3. A method for detecting the presence of melanoma or prostatic cancer in a human host, said method comprising:

combining a sample from said human host with monoclonal antibody 12f3.2 which binds to a surface membrane antigen of melanoma cells or prostatic cancer cells having a molecular weight of about 170 Kd; and detecting formation of immune complexes in said sample as indicative of the presence of melanoma cells or prostatic cancer cells.

4. The method of claim 3 wherein said sample is human tissue.

5. The method of claim 3 wherein said sample is serum.

* * * * *

UNITED STATES PATENT AND TRADEMARK OFFICE
CERTIFICATE OF CORRECTION

PATENT NO. : 6,057,116 Page 1 of 1
DATED : May 2, 2000
INVENTOR(S) : Juergen R. Vielkind It is certified that error appears in the above-identified patent and that said Letters Patent is hereby corrected as shown below:

Title page,
Item [56], References Cited, OTHER PUBLICATIONS, insert -- Siamev, TA, New England J. Medicine 317 (15): 909-16 1987 --
U.S. PATENT DOCUMENTS, delete "4,590,071 5/1986 Scannon, et al."

Column 2,
Line 35, "cher" should read -- Cher --

Column 4,
Line 24, delete 1st instance of "Fig. 1"

Column 8,
Line 18, "Pres,s" should read -- Press --

Column 18,
Lines 36-38, delete 2nd instance of "Intensity of positive XMEL staining was graded as: 1+weak; 2+=moderate;3+=strong; 4+=very strong; hg PIN=high grade prostatic intraepithelial neoplasia."

Column 21,
Line 26, "CPR" should read -- PCR --
Line 42, "P40" should read -- P-40 --
Line 64, "cpatured"should read -- captured --
Line 66, "betwen" should read -- between --

Column 22,
Line 31, "reactvity" should read -- reactivity --

Signed and Sealed this

First Day of October, 2002

Attest:

Attesting Officer

JAMES E. ROGAN
Director of the United States Patent and Trademark Office

SEQUENCE LISTING

<160> NUMBER OF SEQ ID NOS: 10

<210> SEQ ID NO 1
<211> LENGTH: 10
<212> TYPE: PRT
<213> ORGANISM: Unknown
<220> FEATURE:
<223> OTHER INFORMATION: Description of Unknown Organism:Extracellular domain of mrk-receptor protein

<400> SEQUENCE: 1

Leu Phe Arg Ser Glu Asp Gln Ser Ile Glu
 1               5                   10

<210> SEQ ID NO 2
<211> LENGTH: 124
<212> TYPE: DNA
<213> ORGANISM: Unknown
<220> FEATURE:
<223> OTHER INFORMATION: Description of Unknown Organism:Nucleotide sequence of mrk-receptor tyrosine kinase

<400> SEQUENCE: 2
cacgctgcag ctgcgctacg ccaacaccat caactggagg cgcttgttcc ggtctgagga      60
ccagagcata gagtatgacg ccaggactga gaatcaaacc tgcaacaacg agtgctcaga    120
ggat                                                                  124

<210> SEQ ID NO 3
<211> LENGTH: 41
<212> TYPE: PRT
<213> ORGANISM: Unknown
<220> FEATURE:
<223> OTHER INFORMATION: Description of Unknown Organism:Amino acid sequence of mrk-receptor tyrosine kinase from 446-486

<400> SEQUENCE: 3

Thr Leu Gln Leu Arg Tyr Ala Asn Thr Ile Asn Trp Arg Arg Leu Phe
 1               5                  10                  15

Arg Ser Glu Asp Gln Ser Ile Glu Tyr Asp Ala Arg Thr Glu Asn Gln
            20                  25                  30

Thr Cys Asn Asn Glu Cys Ser Glu Asp
        35                  40

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence:XMEL binding epitope

<400> SEQUENCE: 4

Asn Ala Arg Val Cys Asp Phe Pro Gly Ile Ser Cys Val Tyr Arg
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:XMEL binding epitope -continued

```
<400> SEQUENCE: 5

Leu Ser Gly Ser Val Pro Ser Leu Val Ala Pro Tyr Ala Pro Trp
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence:XMEL binding
      epitope

<400> SEQUENCE: 6

Arg Asp Leu Phe Ser Pro Cys Pro Phe Pro Gly Phe Cys Arg Gln
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence:XMEL binding
      epitope

<400> SEQUENCE: 7

Met Thr Gly Asn Ser Cys Gly Asp Phe Pro Ala Tyr Cys Arg Leu
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence:XMEL binding
      epitope

<400> SEQUENCE: 8

Trp Pro Phe Val Asp Glu Pro Gly Leu Ile Arg Leu Pro Ala Ala
 1               5                  10                  15

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence:XMEL binding
      epitope

<400> SEQUENCE: 9

Arg Gly Gly Ser Cys Leu Ala Leu Ser Ser Leu Ala Leu Phe
 1               5                  10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence:XMEL binding
      epitope

<400> SEQUENCE: 10

Gly Gly Phe Pro Gly Leu Met Phe Gly His Ile Cys Ser Asp
 1               5                  10
```